United States Patent [19]
Willick et al.

[11] Patent Number: 5,556,940
[45] Date of Patent: Sep. 17, 1996

[54] PARATHYROID HORMONE ANALOGUES FOR THE TREATMENT OF OSTEOPOROSIS

[75] Inventors: Gordon E. Willick, Orleans; James F. Whitfield, Ottawa; Witold Surewicz, Orleans; Wing L. Sung, Gloucester; Witold Neugebauer, Ottawa, all of Canada

[73] Assignee: National Research Council of Canada, Ottawa, Canada

[21] Appl. No.: 262,495

[22] Filed: Jun. 20, 1994

[51] Int. Cl.$^6$ .................. A61K 38/29; C07K 14/635
[52] U.S. Cl. ........................... 530/317; 530/324
[58] Field of Search ...................... 530/345, 324, 530/317; 514/12, 21, 11

[56] References Cited

U.S. PATENT DOCUMENTS

| | | | |
|---|---|---|---|
| 4,086,196 | 4/1978 | Tregear | 260/112.5 |
| 4,771,124 | 9/1988 | Rosenblatt et al. | 530/324 |

FOREIGN PATENT DOCUMENTS

| | | | |
|---|---|---|---|
| 2100423 | 1/1994 | Canada. | |
| 477885 | 4/1991 | European Pat. Off. | 530/324 |

| | | |
|---|---|---|
| WO93/06845 | 4/1993 | WIPO. |

OTHER PUBLICATIONS

Int. J. Peptide Protein Res., vol. 42, issued 1993, Chorev et al., "Circular dichroism studies of antagonists . . ." pp. 342–345.
Int. J. Peptide Protein Res., vol. 43, issued 1994, Neugebauer et al., "Structure and protein kinase C stimulating activities . . .", pp. 555–562.
J. Endocr., vol. 74, issued 1977, Visser et al., "Immunological Studies on Parathyroid Hormone . . .", pp.461–466.
Endocrinology, vol. 108, No. 1, issued 1981, Bringhurst et al., "Bone Collagen Synthesis in vitro . . .", pp. 103–108.

Primary Examiner—Jeffrey E. Russel

[57] ABSTRACT

Certain analogues of human parathyroid hormone (hPTH) have been found to be effective for the treatment of osteoporosis, while showing decreased side effects. Analogues showing this effect include all sequences from hPTH-(1–28)-$NH_2$ to hPTH-(1–31)-$NH_2$ and all sequences from [$Leu^{27}$]-hPTH-(1–28)-$NH_2$ to [$Leu^{27}$]-hPTH-(1–33)-$NH_2$. Also included are cyclic analogues cyclo($Lys^{26}$-$Asp^{30}$) [$Leu^{27}$]-hPTH-(1–34)$NH_2$ and cyclo ($Lys^{27}$-$Asp^{30}$)-hPTH-(1–34)-$NH_2$. Analogues in the form of the carboxyl terminal amide are particularly effective.

2 Claims, 3 Drawing Sheets

Fig. 1

H₂N-Ser-Val-Ser-Glu-Ile-Gln-Leu-Met-His-Asn-Leu-Gly-Lys-His-
Leu-Asn-Ser-Met-Glu-Arg-Val-Glu-Trp-Leu-Arg-Lys-Lys-Leu-Gln-
Asp-Val-His-Asn-Phe-CONH₂ [SEQ ID NO: 1]

Fig. 2

H₂N-Ser-Val-Ser-Glu-Ile-Gln-Leu-Met-His-Asn-Leu-Gly-Lys-His-
Leu-Asn-Ser-Met-Glu-Arg-Val-Glu-Trp-Leu-Arg-Lys-Lys-Leu-Gln-
Asp-Val-CONH₂ [SEQ ID NO: 3]

Fig. 3

H₂N-Ser-Val-Ser-Glu-Ile-Gln-Leu-Met-His-Asn-Leu-Gly-Lys-His-
Leu-Asn-Ser-Met-Glu-Arg-Val-Glu-Trp-Leu-Arg-Lys-Leu-Leu-Gln-
Asp-Val-CONH₂ [SEQ ID NO: 4]

Fig. 4

H₂N-Ser-Val-Ser-Glu-Ile-Gln-Leu-Met-His-Asn-Leu-Gly-Lys-His-
Leu-Asn-Ser-Met-Glu-Arg-Val-Glu-Trp-Leu-Arg-Lys-Lys-Leu-Gln-
Asp-CONH₂ [SEQ ID NO: 5]

Fig. 5

H₂N-Ser-Val-Ser-Glu-Ile-Gln-Leu-Met-His-Asn-Leu-Gly-Lys-His-
Leu-Asn-Ser-Met-Glu-Arg-Val-Glu-Trp-Leu-Arg-Lys-Leu-Leu-Gln-
Asp-CONH₂ [SEQ ID NO: 6]

Fig. 6

H₂N-Ser-Val-Ser-Glu-Ile-Gln-Leu-Met-His-Asn-Leu-Gly-Lys-His-Leu-
Asn-Ser-Met-Glu-Arg-Val-Glu-Trp-Leu-Arg-Lys-Leu-Leu-Gln-Asp-
Val-His-Asn-Phe-CONH₂ [SEQ ID NO: 2]

Fig. 7

H₂N-Ser-Val-Ser-Glu-Ile-Gln-Leu-Met-His-Asn-Leu-Gly-Lys-His-Leu-
Asn-Ser-Met-Glu-Arg-Val-Glu-Trp-Leu-Arg-Lys-Lys-Leu-Gln-Asp-
Val-His-Asn-Phe-CONH₂ [SEQ ID NO: 1]

PARATHYROID HORMONE ANALOGUES FOR THE TREATMENT OF OSTEOPOROSIS

FIELD OF THE INVENTION

This invention relates to analogues of human parathyroid hormone, which have been found to be effective in the treatment of osteoporosis and will reverse the loss of bone and increase bone mass and density specifically without undesirable side effects.

BACKGROUND OF THE INVENTION

Osteoporosis is a leading cause of disability in the elderly, particularly elderly women. It is well known that human parathyroid hormone (hPTH) and certain analogues are useful in the treatment of osteoporosis.

Parathyroid hormone (PTH) is produced by the parathyroid gland and is involved in the control of calcium levels in blood. It is a hypercalcemic hormone, elevating blood calcium levels. PTH is a polypeptide and synthetic polypeptides containing the first thirty-four residues of PTH may be prepared using the method disclosed by Erickson and Merrifield, *The Proteins*, Neurath et al., Eds., Academic Press, New York, 1976, page 257, preferably as modified by the method of Hodges et al., *Peptide Research*, 1, 19 (1988).

When serum calcium is reduced to below a "normal" level, the parathyroid gland releases PTH and resorption of bone calcium and increased absorption of calcium from the intestine, as well as renal reabsorption of calcium, occur. The antagonist of PTH is calcitonin, which acts to reduce the level of circulating calcium. Osteoporosis is a progressive disease which results in the reduction of total bone mass. This often results in fractures of load-bearing bones and the physical degenerations characteristic of immobilizing injuries. Osteoporosis is associated with hyperthyroidism, hyperparathyroidism, Cushings syndrome and the use of certain steroidal drugs. Remedies historically have involved increase in dietary calcium, estrogen therapy and increased doses of vitamin D.

Although high levels of PTH can remove calcium from the bone, low doses can actually promote bone growth.

While the use of PTH is effective in the treatment of osteoporosis by diminishing the loss of bone mass, PTH may exhibit other undesired pharmalogical effects, such as hypertension and smooth muscle relaxation (e.g. relaxation of gastrointestinal organs, uterus, tracheal and vas deferens as well as positive chronotropic and inotropic effects on the heart.

Tregear U.S. Pat. No. 4,086,196, describes human PTH analogues and claims that the first 27 to 34 amino acids are the most effective in terms of activation of adenylyl cyclase. Rosenblatt et al, U.S. Pat. No. 4,771,124 discloses the property of hPTH analogues wherein $Trp^{23}$ is substituted by amino acids phenylalanine, leucine, norleucine, valine, tyrosine, beta-naphthylalanine and alpha-naphthylalanine as a PTH antagonist. These modified hPTH analogues also have the 2 and 6 amino terminal amino acids removed, resulting in loss of most agonist activities when used to treat osteoporosis.

Pang et al WO93/06845, published Apr. 15, 1993, describes analogues of hPTH which involve substitutions of $Arg^{25}$, $Lys^{26}$, $Lys^{27}$ with numerous amino acids, including alanine, asparagine, aspartic acid, cysteine, glutamine, glutamic acid, glycine, histidine, isoleucine, leucine, methionine, phenylalanine, proline, serine, threonine, tryptophan, tyrosine or valine. These are claimed to be effective in the treatment of osteoporosis with minimal effects on blood pressure and smooth muscle.

The biological activity of hPTH is reflected in the activation of two second messenger systems, G-protein coupled adenylyl cyclase (cAMPase) and cAMPase coupled and uncoupled protein kinase C(PKC) activity. It has been established that the increase in bone growth, i.e. that effect which is useful in the treatment of osteoporosis, is coupled to the ability of the peptide sequence to increase cAMPase activity. The native hPTH containing only the first 34 amino acids has been shown to have all activities. It is typically shown as:

| Ser 1 | Val | Ser | Glu | Ile 5 | Gln | Leu | Met | His | Asn 10 | A |
|---|---|---|---|---|---|---|---|---|---|---|
| Leu | Gly | Lys | His | Leu 15 | Asn | Ser | Met | Glu | Arg 20 | |
| Val | Glu | Trp | Leu | Arg 25 | Lys 26 | Lys 27 | Leu | Gln | Asp 30 | |
| Val | His | Asn | Phe | (SEQ ID NO:1) | | | | | | |

It is the object of the present invention to produce new hPTH analogues having increased cAMPase activity with minimal side effects.

BRIEF SUMMARY OF THE INVENTION

The above molecule "A" may have either a free carboxyl or amide ending in the sequence.

According to one feature of the present invention, it has been found that the cAMPase independent PKC is restricted to the 28–34 region of the above molecule "A". On the other hand, cAMPase activity has been shown to require the first 30 residues of the molecule. Thus, in accordance with this embodiment of the invention, it is possible to remove those biological activities associated with the cAMPase independent PKC activity by deleting a selected terminal portion of the hPTH-(1–34) molecule. In order for these shortened analogues to exhibit maximum activity, they must be in the form of the carboxyl terminal amides. One feature of the invention therefore comprises the human parathyroid analogues hPTH-(1–28)-$NH_2$, hPTH-(1–29)-$NH_2$, hPTH-(1–30)-$NH_2$ and hPTH-(1–31)-$NH_2$.

According to another feature of the present invention, it has surprisingly been found that simply replacing $Lys^{27}$ with a Leu in the above molecule "A" is capable of increasing binding to the receptor and results in a higher activity for cAMPase stimulation. This analogue also exhibits its maximum activity only when in the form of the carboxyl terminal amide. Thus, another feature of the invention comprises human parathyroid analogues including all sequences from [Leu27]-hPTH-(1–28)-$NH_2$ to [$Leu^{27}$]-hPTH-(1–33)-$NH_2$.

It is believed that this activity relating to $Lys^{27}$ is because of an amphiphilic α-helix near the carboxyl terminus of the above molecule is essential for the binding of hPTH to its receptor such as to stimulate cAMPase activity. This amphiphilic α-helix includes residues 20–34, with the most stable helix being between residues 20 and 29. In receptor peptide complexes, where the bound peptide is in an α-helical conformation, the hydrophobic face is bound to the receptor. It is believed that $Lys^{27}$ is a single polar residue on the hydrophobic phase of this supposed helix and that the increased binding is achieved by replacing the $Lys^{27}$ with another amino acid.

A further feature of the invention comprises cyclic analogues based on the above molecule "A". These are in the form of lactams, along the polar face of the helix. As with the above features of the invention, the cyclic analogues are also most effective when in the form of carboxyl terminal amides and provide improved activity and/or stability. The cyclic analogues include cyclo (Lys$^{26}$-Asp$^{30}$) [Leu$^{27}$]-hPTH-(1–34)-NH$_2$ and cyclo (Lys$^{27}$-Asp$^{30}$)-hPTH-(1–34)-NH$_2$.

BRIEF DESCRIPTION OF THE DRAWINGS

FIG. 1 shows the structure of an amidated fragment of natural human PTH containing 34 residue (SEQ ID NO: 1)

FIG. 2 shows the structure of hPTH-(1–31)-NH$_2$ (SEQ ID NO: 3)

FIG. 3 shows the structure of [Leu$^{27}$]-hPTH-(1–31)-NH$_2$ (SEQ ID NO: 4)

FIG. 4 shows the structure of hPTH-(1–30)-NH$_2$ (SEQ ID NO: 5)

FIG. 5 shows the structure of [Leu$^{27}$]-hPTH-(1–30)-NH$_2$ (SEQ ID NO: 6)

FIG. 6 shows the structure of cyclo (Lys$^{26}$-Asp$^{30}$) [Leu$^{27}$]-hPTH-(1–34)-NH$_2$ (SEQ ID NO: 2)

FIG. 7 shows the structure of cyclo (Lys$^{27}$-Asp$^{30}$)-hPTH-(1–34)-NH$_2$ (SEQ ID NO: 1)

DESCRIPTION OF THE PREFERRED EMBODIMENTS

Figure 8A:
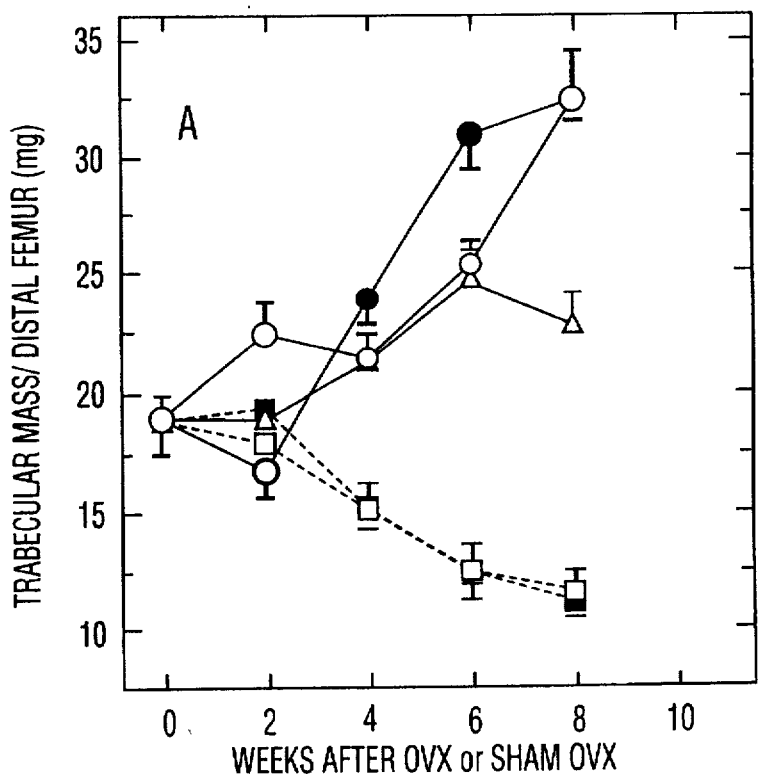
FIG. 8A shows trabecular mass data for hPTH analogues of the invention.
Figure 8B:
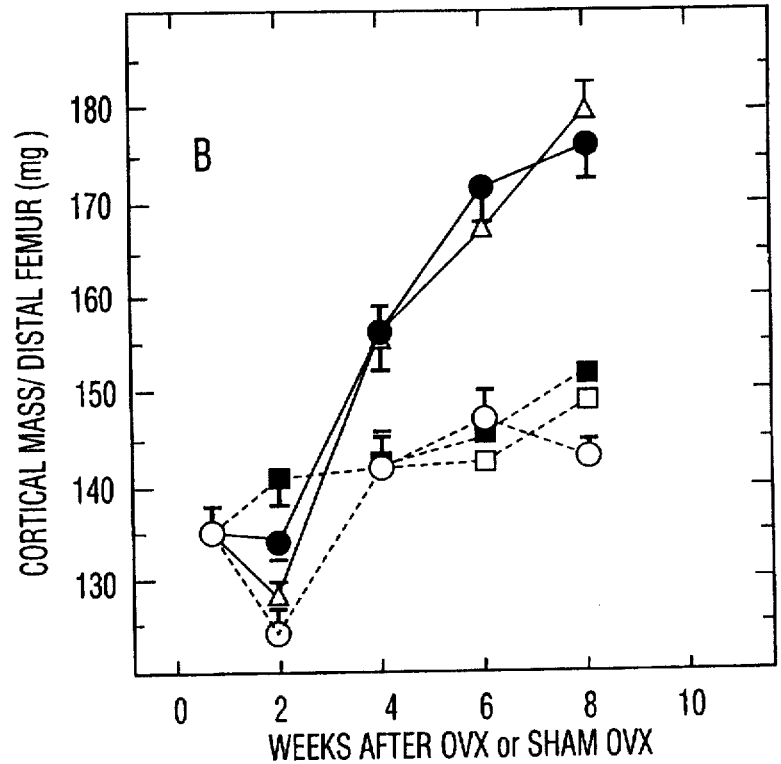
FIG. 8B shows cortical mass data for hPTH analogues of the invention.
Figure 9A:
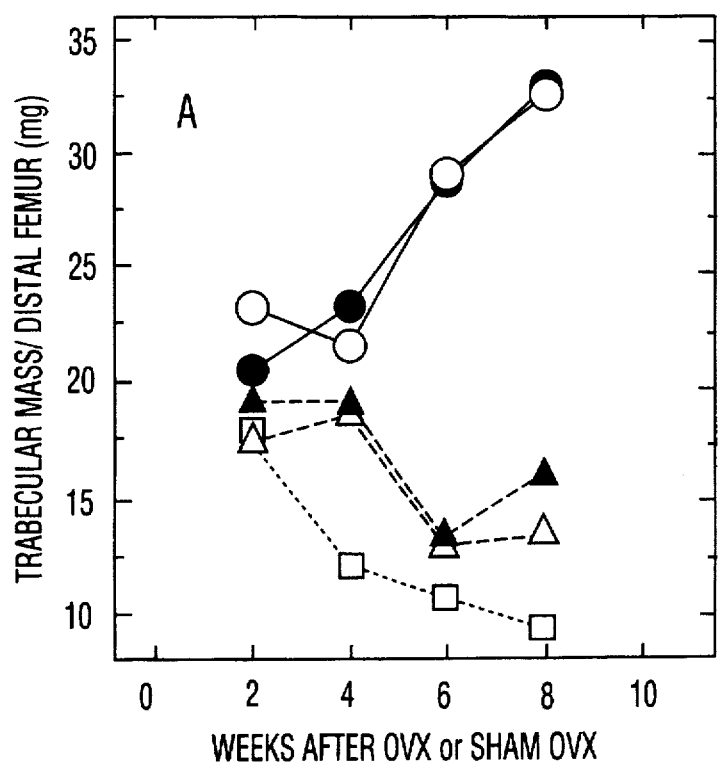
FIG. 9A shows further trabecular mass data of the invention.
Figure 9B:
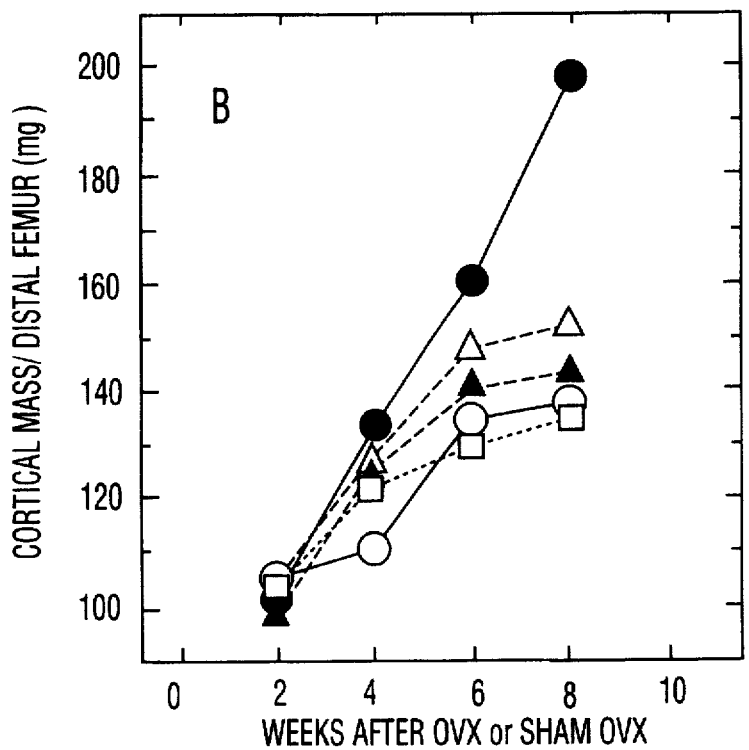
FIG. 9B shows further cortical mass data of the invention.

The structure of human parathyroid hormone (hPTH) is shown in FIG. 1 (SEQ ID NO: 1). Representative synthetic analogues are described in Table 1 and are further shown in FIG. 2–7 and SEQ ID NO: 2–SEQ ID NO: 6. Trabecular and cortical mass data for various of these analogues is shown in FIGS. 8A, 8B, 9A and 9B.

Preparation of Hormone Analogues

The technique of solid phase synthesis developed by R. B. Merrifield ("Solid-Phase Peptide Synthesis", Advanced in Enzymology, 32, 221–296 (1969)), incorporated herein by reference, is widely and successfully used for the synthesis of polypeptides such as parathyroid hormone. The strategy is based on having the carboxyl-terminus amino acid of the support attached to a solid support. Successive amino acids are then added in very high yield. The α-amino group is protected in such a way that this protecting group can be removed without the removal of groups protecting side-chain reactive groups of the peptide from the solid support. The chemistry used here involves a modification of the original Merrifield method, referred to as the Fmoc approach. The Fmoc (fluorenylmethoxycarbonyl) group can be removed by mild alkaline conditions which leave the alkali stable side-chain protecting groups and the link to the support untouched. This technique is described by E. Atherton & R. C. Sheppard (1989), "Solid Phase Peptide Synthesis: a Practical Approach", IRL Press, New York, N.Y., incorporated herein by reference.

EXAMPLE 1

Synthesis & Purification of Linear hPTH Analogues

The α-amino groups of the amino acids were protected with 9-Fluorenyl-methoxycarbonyl (Fmoc) during coupling. Couplings were performed with a mixture of hydroxybenzotriazole (HOBT), 2-(1H-Benzotriazole-1-yl)-1,1,3,3-tetramethyluronium tetrafluoroborate (TBTU), and diisopropylethylamine (DIPEA). A 4-fold excess of activated amino acids was used with double coupling on addition of the Asn, Gln, His, Val, and Ile residues. The coupling times for Arg and Gly additions were increased from 30 min. to 60 min. Side chain protection of the amino acids was provided by: (1) the ε-amino group of lysine was protected as the 2-chlorobenzyloxycarbonyl derivative; (2) the guanido group of arginine was protected as the methoxytrimethylphenylsulfonyl derivative; (3) the carboxyl groups of glutamic and aspartic acids were protected as the t-butyl esters; (4) the hydroxyl group of serine was protected as the t-butyl ether; (5) the imidazole nitrogen of histidine was protected as the trityl derivative; (6) the amide nitrogens of glutamine and asparagine were protected as the trityl derivatives. Amino acid derivatives were purchased from Bachem Chemicals California. Analogues were synthesized with a Milligen 9050 Plus continuous-flow peptide synthesizer on TentaGel S-RAM as the solid support. Cleavage from the support yielded the terminal carboxylamide derivative as the product. Syntheses to yield the free carboxyl terminus were carried out with the appropriate Fmoc amino acyl derivative of Nova Syn TGA resin (Nova Biochemicals). For example, the synthesis of [Asp$^{35}$]-hPTH-(1–35)-COOH began with Fmoc-Asp(OtBu) Nova Syn TGA as the support.

Simultaneous cleavage from the solid support was carried out with 95% TFA in the presence of 6% thioanisole, 6% phenol, and 3% 1,2-ethanedithiol. The crude peptide was then precipitated with diethylether and lyophilized.

The crude product was purified by HPLC on a semi-prep PLRP-S column (Polymer Laboratories) (7.5×300 mm, 10 μm), using 1%/min gradient of 0.1% trifluoroacetic acid in acetonitrile into 0.1% trifluoroacetic acid in water.

EXAMPLE 2

Synthesis and Purification of Cyclic Analogues

Cyclo(Lys$^{26}$-Asp$^{30}$) [Leu$^{27}$]-hPTH-(1–34)-NH$_2$. The synthesis was performed similarly to Example 1 except in the region of the lactam. The side chain carboxyl group of Asp$^{30}$ was protected temporarily as the t-butyl ester. The side chain amino group of Lys was protected as the t-butyloxycarbonyl derivative. The coupling of Lys$^{26}$ was accomplished outside of the synthesizer. The resin was swollen in dichloromethane and the t-butyl group of Asp$^{30}$ and t-butyloxycarbonyl group of Lys$^{26}$ were removed by treatment with 30% trifluoroacetic acid in dichloromethane for 15 min. The resin was washed with dichloromethane, dimethylformamide, and dichloromethane in turn, neutralized with 20% diisopropylethylamine, then washed again with dichloromethane, dimethylformamide, and dichloromethane. The peptide-resin was then returned to the synthesizer and cyclization was accomplished by 2 cycles of 3 hr each of (benzotriazolyl)-N-oxy-pyrrolidinium phosphonium hexafluorophosphate (PyBOP)/diisopropyethylamine/dimethylformamide (1:1:1) in 8-fold excess. Completeness of the reaction was monitored by a ninhydrin assay, as described in Kaiser et al (1970), Anal. Biochem. 34, 595–598, incorporated herein by reference. Following lactam formation, any free residual amino groups were capped using acetic anhydride and 2-(1H-Benzotriazole-1-yl)-1,1,3,3-tetramethyluronium tetrafluoroborate/diisopropylamine in dimethylformamide.

Cyclo-(Lys$^{27}$-Asp$^{30}$)-hPTH-(1-34)-NH$_2$—The synthesis was carried out in an analogous manner to that described above for cyclo(Lys$^{26}$-Asp$^{30}$)[Leu$^{27}$]-hPTH-(1-34)-NH$_2$, using OtBu protection of Asp-30 and t-butyloxycarbonyl protection of Lys$^{27}$.

EXAMPLE 3

Adenylyl Cyclase Assays

The ability of hPTH analogues to bind to receptors and activate the adenylyl cyclase coupled signalling mechanism was carried out on a differentiation competent osteoblast-like ROS 17/2 rat osteosarcoma cell line. Adenylyl cyclase activity was estimated by prelabelling the cellular ATP pool with [$^3$H]-adenine and then measuring the amount of [$^3$H]-cyclic AMP produced from the [$^3$H]-ATP during the first 10 min. of exposure to a particular analogue. This was based on the procedures described by Whitfield et al (1992), J. Cell Physiol. 150, 299–303, incorporated herein by reference.

The adenylyl cyclase assay results are expressed in Table 1 below as the concentration necessary to express a half-maximal increase in the adenylyl cyclase activity.

TABLE 1

| | Analogue | $C_{50\% \, max}$ (adenylyl cyclase), nM |
|---|---|---|
| 1 | hPTH-(1–34)-NH$_2$ | 15 |
| 2 | hPTH-(1–31)-NH$_2$ | 20 |
| 3 | [Leu$^{27}$]-hPTH-(1–31)-NH$_2$ | 14 |
| 4 | hPTH-(1–30)-NH$_2$ | 21 |
| 5 | [Leu$^{27}$]-hPTH-(1–30)-NH$_2$ | 15 |
| 6 | c(Leu$^{26 \cdot Asp30}$)[Leu$^{27}$]-hPTH-(1–34)-NH$_2$ | 7 |
| 7 | c(Lys$^{27}$-Asp$^{30}$)-hPTH-(1–34)-NH$_2$ | 29 |
| 8 | hPTH-(1–29)-NH$_2$ | 28 |
| 9 | hPTH-(1–29)-NH$_2$ | 32 |

EXAMPLE 4

Determination of Anabolic Activities of hPTH Analogues with Ovariectomized Rat Model A full description of the protocol is given in Rixon et al (1994), J. Bone, 9, 1179–1189, incorporated herein by reference. Sprague-Dawley rats weighing 255–275 g were purchased from Charles River (St. Constant, QC, Canada). For each experiment, 105 rats were weighed and divided into 21 groups, each with 5 rats, with comparable mean body weights between 260 and 265 g. These 21 groups were divided into 6 experimental groups consisting of 1 group of 5 animals for O-time controls and 5 groups of 20 rats each which provided one group for normal or sham-ovariectomized (Sham-OVX) controls, one for OVX controls, and 3 for OVX rats treated with various hPTH analogues.

Sham OVX and OVX were performed under fluothane anesthesia by the standard dorsal approach. For sham-OVX, the varies were exteriorized, but not removed. Except for the normal, unoperated rats, day 0 for each experimental group was the day of OVX. Starting 2 weeks later, designated groups of rats were given daily subcutaneously injections of PTH analogues (1 nmole/100g of body weight) dissolved in acidic saline (0.15M NaCl containing 0.001N HCl). The OVX control animals received comparable volumes of diluent solution only.

All animals survived the Sham-OVX and OVX operations, and there were no unscheduled deaths in any groups during the following 8 weeks.

The preparation and analysis of cortical and trabecular bone was carried out as described in M. Gunness-Hey & J. M. Hock (1984), Metab. Bone Dis. Rel. Res., 5, 177–181, incorporated herein by reference. Femurs were isolated, cleaned, and their lengths from the proximal, collum femoris to the distal condylar surfaces were measured. Each bone was then cut in half at mid-diaphysis and the proximal half discarded. After removing the epiphysis, each half-femur was split lengthwise and the marrow washed out with distilled water. Each half was placed under a dissecting microscope and the trabecular (cancellous) bone was scraped out. The isolated trabecular bone and the remaining cortical (compact bone) were dried at 55° C. for at least 24 hr., and weighed to determined dry mass, expressed as mg/distal half-femur.

After at least 3 days, the trichloroacetic acid extract was quantitatively removed and saved. The calcium contents of the pooled trichloroacetic acid extracts from each cortical and trabecular bone sample were measured using the o-cresolphthalein complexone colorimetric procedure, using a kit from CIBA-Corning Diagnostics.

The results obtained are shown in FIGS. 8 and 9. Parts A and B of FIG. 8 shows the trabecular (A) and cortical mass (B) data for various hPTH analogues tested in the ovariectomized rat model (Example 4), in which hPTH-(1–34)NH$_2$ (closed circles); sham OVX (open circles); hPTH-(1–31)-NH$_2$ (open triangles); OVX (open squares); hPTH-(8–84)-NH$_2$, a PTH analogue lacking adenylyl cyclase activity (closed squares).

Further trabecular and cortical data is shown in parts A and B of FIG. 9, in which hPTH-(1–34)-NH$_2$ (closed circles); sham OVX (open circles); OVX (open squares); hPTH-(1–30)-COOH, 5 nmols/100 g of rat dose (closed triangles); hPTH-(1–30)COOH, 3 nmoles/100 g dose (open triangles).

The analogues of the present invention can be used in the treatment of osteoporosis and other bone related diseases and disorders involving bone cell calcium regulation.

The analogues of the present invention may be administered to a warm-blooded mammalian in need thereof, particularly a human, by parenteral, topical, rectal administration or by inhalation. The analogues may be conventionally formulated in a parenteral dosage form compounding about 1 to about 300 mg per unit of dosage with a conventional vehicle, excipient, binder, preservative, stabilizer, color, agent or the like as called for by accepted pharmaceutical practice.

For parenteral administration, a 1 to 10 ml intravenous, intramuscular or subcutaneous injection would be given one to four times daily. The injection would contain an analogue of the present invention in an aqueous isotonic sterile solution or suspension optionally with a preservative such as phenol or a solubilizing agent such as ethylenediaminetetraacetic acid (EDTA). Among the acceptable vehicles and solvents that may be employed are water, Ringer's solution and isotonic sodium chloride solution. In addition, sterile, fixed oils are conventionally employed as a solvent or suspending medium. Synthetic monoglycerides, diglycerides, fatty acids (such as oleic acid) find use as fixed oil in the preparation of injectables.

For rectal administration, the analogues of the present invention can be prepared in the form of suppositories by mixing with a suitable non-irritating excipient such as cocoa butter or polyethylene glycols.

For topical use, the analogues of the present invention can be prepared in the form of ointments, jellies, solutions, suspensions or dermal adhesive patches.

Daily doses are in the range of about 0.01 to about 200 mg per kg of body weight, depending on the activity of the specific compound, the age, weight, sex and conditions of the subject to be treated, the type and severity of the disease, the frequency and route of administration. As would be well known, the amount of active ingredient that may be combined with the carried materials to produce a single dosage will vary depending upon the host treated and the particular mode of administration.

We claim:

1. A human parathyroid hormone analogue (hPTH) comprising hPTH-(1–31)-NH$_2$.

2. A cyclic analogue of a human parathyroid hormone selected from the group consisting of cyclo(Lys26-Asp$^{30}$) [Leu$^{27}$]-hPTH-(1–34)-NH$_2$ and cyclo (Lys$^{27}$-Asp$^{30}$)-hPTH-(1–34)-NH$_2$.

* * * * *

UNITED STATES PATENT AND TRADEMARK OFFICE
Certificate

Patent No. 5,556,940                                                                  Patented: September 17, 1996

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Gordon E. Willick, Orleans, Canada; James F. Whitfield, Ottawa, Canada; Witold Surewicz, Orleans, Canada; Wing L. Sung, Gloucester, Canada; Witold Neugebauer, Ottawa, Canada; and Raymond H. Rixon, Ottawa, Canada.

Signed and Sealed this Twenty-eighth Day of June 2005.

*BRUCE CAMPELL*
*Supervisory Patent Examiner*
Art Unit 1654

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
        ( A ) LENGTH: 34 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 1:

```
Ser  Val  Ser  Glu  Ile  Gln  Leu  Met  His  Asn  Leu  Gly
 1              5                        10
Lys  His  Leu  Asn  Ser  Met  Glu  Arg  Val  Glu  Trp  Leu
          15                       20
Arg  Lys  Lys  Leu  Gln  Asp  Val  His  Asn  Phe
25                  30
```

( 2 ) INFORMATION FOR SEQ ID NO: 2:

( i ) SEQUENCE CHARACTERISTICS:
        ( A ) LENGTH: 34 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 2:

```
Ser  Val  Ser  Glu  Ile  Gln  Leu  Met  His  Asn  Leu  Gly
 1              5                        10
Lys  His  Leu  Asn  Ser  Met  Glu  Arg  Val  Glu  Trp  Leu
          15                       20
Arg  Lys  Leu  Leu  Gln  Asp  Val  His  Asn  Phe
25                  30
```

( 2 ) INFORMATION FOR SEQ ID NO: 3:

( i ) SEQUENCE CHARACTERISTICS:
        ( A ) LENGTH: 31 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 3:

```
Ser  Val  Ser  Glu  Ile  Gln  Leu  Met  His  Asn  Leu  Gly
 1              5                        10
Lys  His  Leu  Asn  Ser  Met  Glu  Arg  Val  Glu  Trp  Leu
          15                       20
Arg  Lys  Lys  Leu  Gln  Asp  Val
25                  30
```

( 2 ) INFORMATION FOR SEQ ID NO: 4:

( i ) SEQUENCE CHARACTERISTICS:
        ( A ) LENGTH: 31 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 4:

```
Ser  Val  Ser  Glu  Ile  Gln  Leu  Met  His  Asn  Leu  Gly
 1                   5                           10
Lys  His  Leu  Asn  Ser  Met  Glu  Arg  Val  Glu  Trp  Leu
              15                      20
Arg  Lys  Leu  Leu  Gln  Asp  Val
 25                   30
```

( 2 ) INFORMATION FOR SEQ ID NO: 5:

( i ) SEQUENCE CHARACTERISTICS:
        ( A ) LENGTH: 30 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 5:

```
Ser  Val  Ser  Glu  Ile  Gln  Leu  Met  His  Asn  Leu  Gly
 1                   5                           10
Lys  His  Leu  Asn  Ser  Met  Glu  Arg  Val  Glu  Trp  Leu
              15                      20
Arg  Lys  Lys  Leu  Gln  Asp
 25                   30
```

( 2 ) INFORMATION FOR SEQ ID NO: 6:

( i ) SEQUENCE CHARACTERISTICS:
        ( A ) LENGTH: 30 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 6:

```
Ser  Val  Ser  Glu  Ile  Gln  Leu  Met  His  Asn  Leu  Gly
 1                   5                           10
Lys  His  Leu  Asn  Ser  Met  Glu  Arg  Val  Glu  Trp  Leu
              15                      20
Arg  Lys  Leu  Leu  Gln  Asp
 25                   30
```